United States Patent [19]

Jamison et al.

[11] 4,262,539
[45] Apr. 21, 1981

[54] DRIVE ASSEMBLY FOR PROBE CARRIER

[75] Inventors: Thomas D. Jamison, Fort Oglethorpe, Ga.; Frank T. Radcliff, Chattanooga, Tenn.

[73] Assignee: Electric Power Research Institute, Palo Alto, Calif.

[21] Appl. No.: 58,008

[22] Filed: Jul. 16, 1979

[51] Int. Cl.³ ............................................. G01N 29/04
[52] U.S. Cl. ..................................... 73/622; 414/745
[58] Field of Search ................. 73/622; 414/757, 745, 414/431, 432; 198/694, 695, 780, 788, 791, 803; 15/159 A, 179

[56] References Cited

U.S. PATENT DOCUMENTS

| 526,362 | 9/1994 | Bicknell | 15/179 X |
| 843,222 | 2/1907 | Luther | 15/179 X |
| 2,301,809 | 11/1942 | Ovalle | 15/179 X |
| 3,239,276 | 3/1966 | Charvat | 15/179 X |

*Primary Examiner*—Jerry W. Myracle
*Attorney, Agent, or Firm*—Flehr, Hohbach, Test

[57] ABSTRACT

A drive assembly for a probe carrier such as used for inspection and maintenance of a heat exchanger in a steam driven electric power generation plant includes a motor and speed reducer and drive wheel for pushing a probe carrier through the tubes of the heat exchanger. The carrier may comprise nylon tubing, and the drive wheel includes radially mounted wires with the tips of the wires defining a surface for engaging the tubing. An adjustable pressure plate yieldably biases the tubing into engagement with the drive wheel with sufficient pressure for the wire tips to indent the tubing surface but without penetrating the tubing surface whereby an interference drive of the probe carrier is achieved.

12 Claims, 5 Drawing Figures

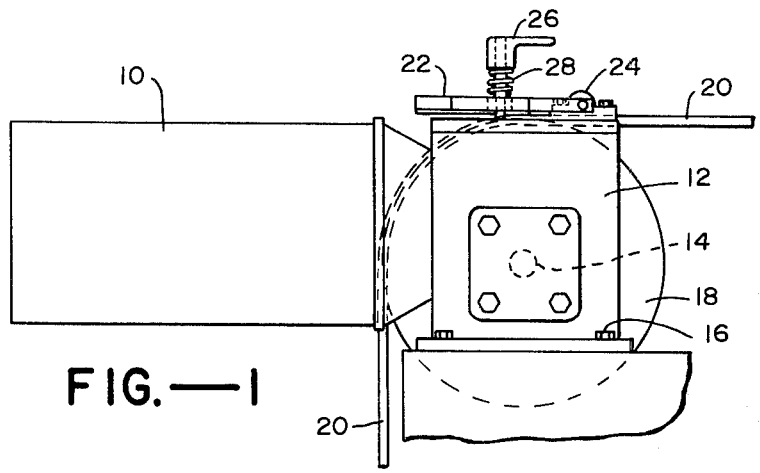
FIG.—1
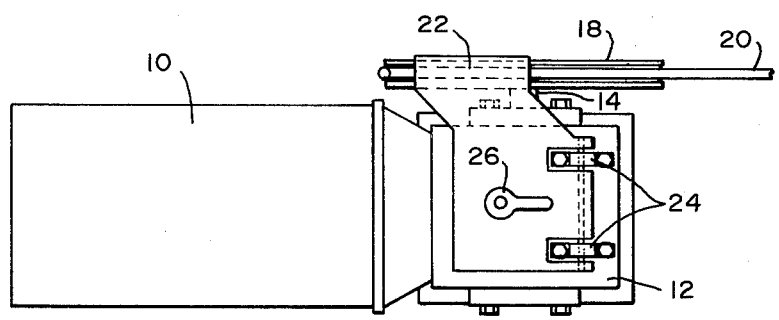
FIG.—2
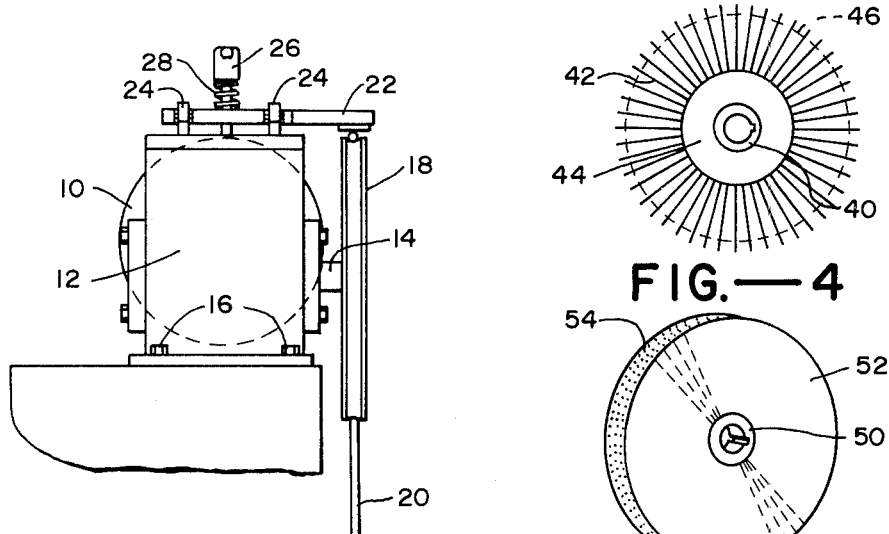
FIG.—3
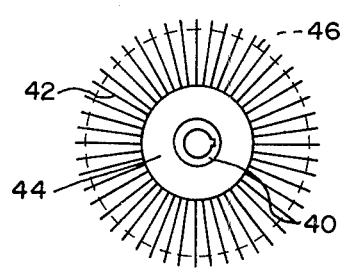
FIG.—4
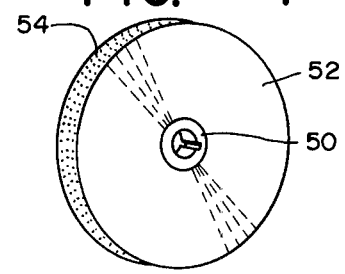
FIG.—5

DRIVE ASSEMBLY FOR PROBE CARRIER

This invention relates generally to inspection equipment for tubular products such as coils in heat exchanger, and more particularly the invention relates to an improved drive assembly for positioning probes and probe carriers during the inspection and maintenance of tubular products.

Heat exchangers such as used in connection with steam driven electric power generators are subjected to very high temperatures and pressures. Further, deposits of impurities from the fluids used in the heat exchangers tend to build up on the tubes and supports in the heat exchanger which can lead to tube thinning and cracking. Thus, the tubes must be periodically inspected to ensure safe operation.

Heretofore, inspection probes have been mounted on flexible tubular carriers with the carriers being pushed by a drive assembly typically including a smooth friction drive mechanism. Such drive assemblies have been relatively complex in structure and susceptible to water, dust, and other lubricants which adversely affect the friction drive.

Accordingly, an object of the present invention is an improved drive assembly for a probe carrier and the like.

Another object of the invention is a drive assembly which provides an interference motive force to a carrier.

Still another object of the invention is a drive assembly which is simple in structure.

Briefly, a drive assembly in accordance with the invention includes a motor, means for coupling said motor to a drive shaft, a drive wheel mounted on said shaft and having a peripheral surface for engaging the probe carrier.

In accordance with one feature of the invention, the peripheral surface for engaging the probe carrier is defined by a plurality of wires radially mounted on the wheel. Preferably, the peripheral surface is contoured to conform to the surface of the probe carrier.

Means is provided for urging the probe carrier into engagement with the peripheral surface. Preferably, this means includes a pressure plate which is mounted to the motor and coupling means with means provided for yieldably biasing the pressure plate into engagement with a probe carrier positioned between the plate and drive wheel. The pressure plate preferably has a contoured low friction bearing surface which engages the probe carrier. By adjusting the pressure from the plate, the tips of wires in contact with the probe carrier will not penetrate or abrade the carrier but will indent or knurl the carrier to provide the interference drive. Accordingly, the drive is not affected by contaminants which can operate as lubricants in a friction drive.

The invention and objects and features thereof will be more readily apparent from the following detailed description and appended claims when taken with the drawings.

Referring now to the drawings,

FIGS. 1, 2, and 3 are top, side, and end views, respectively, of a drive assembly in accordance with one embodiment of the present invention.

FIG. 4 is an end view of one embodiment of a partially disassembled drive wheel in accordance with one embodiment of the present invention.

FIG. 5 is a perspective view of another embodiment of a drive wheel in accordance with the present invention.

Referring now to the drawings, FIG. 1 is a top view of one embodiment of a drive assembly in accordance with the present invention, and FIGS. 2 and 3 are side views and end views, respectively, of the drive assembly. The assembly includes a motor 10 which is mounted to a speed reducer 12 having a drive shaft 14. As shown in FIGS. 2 and 3, the speed reducer 12 is mounted to a suitable support by means of bolts 16.

Mounted to shaft 14 of the speed reducer 12 is a drive wheel 18 which preferably has a contoured peripheral surface for receiving a probe carrier 20. Probe carrier 20 may comprise a nylon tube with the inspection probe mounted on one end thereof. The drive assembly moves the probe through a tubular product by pushing the carrier tubing 20.

Mounted on the top of speed reducer 12 is a pressure plate 22 which is pivotally mounted by means of pillow block bearings 24. Plate 22 preferably has a contoured bottom surface for engaging probe carrier 20, and pressure plate 22 is yieldably biased in engagement with the probe carrier 20 by means of a load adjust mechanism including an adjusting bolt 26 and spring 28 positioned between the handle of the adjusting bolt 26 and pressure plate 22. Thus, by adjusting the position of bolt 26 the tension of spring 28 and consequently the pressure exerted by plate 22 can be adjusted.

In accordance with one feature of the present invention, the drive wheel 18 comprises a plurality of radially mounted wires with the ends of the wires trimmed to define the contour on the peripheral surface for engaging tube 20. Advantageously, by adjustment of the pressure exerted by pressure plate 22, the tips of the wires in contact with the probe carrier do not penetrate or abrade the carrier tube but do indent or knurl the carrier tube to provide an interference drive. Thus, the presence of water, dust, or other lubricants which can greatly reduce the ability of friction drives have negligible influence on the interference drive of the disclosed assembly.

FIG. 4 is an end view of a partially disassembled drive wheel in accordance with one embodiment of the present invention. The wheel includes a hub 40 with a plurality of steel wires 42 mounted thereon. In this embodiment the ends of the wires 42 nearest to hub 40 are mounted in an adhesive 44 such as epoxy or polyurethane resin with circular discs mounted on either side of the wires for maintaining lateral positioning of the wires. One disc is illustrated by the dotted line 46 while the other disc is removed for illustration purposes. The tips of the wires which define the peripheral surface for engaging the probe carrier extend beyond the discs, as shown.

FIG. 5 is a perspective view of another embodiment of a drive wheel in accordance with the present invention. Again, the wheel includes a hub 50 with a plurality of wires 52 extending radially outwardly from hub 50. In this embodiment the entire length of the wires is embedded in an adhesive with only the tips 54 of the wires which define the peripheral surface being exposed. Greater pressure can be exerted against a probe carrier using the drive wheel of FIG. 5 due to the entire length of wires being molded in adhesive. Further, since only the tip portion of the wires is exposed the indentation of the probe carrier by the wires is limited thus minimizing the possibility of the wires penetrating and abrading the probe carrier.

In one embodiment of a drive assembly in accordance with the invention a three-fourths horse power Reliance EF 56 DC motor was used with a Reliance D200 speed reducer. The drive wheel utilized steel wire and the probe carrier comprised nylon tubing. The pressure plate was provided with a Teflon bearing surface to provide low friction through the carrier engaging surface.

While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A drive assembly for a probe carrier such as used for inspection and maintenance of tubular products comprising a motor, means for coupling said motor to a drive shaft, a drive wheel mounted on such shaft, said drive wheel having peripheral surface for engaging a probe carrier with said peripheral surface defined by a plurality of wires radially mounted on said wheel, and means for urging a probe carrier into engagement with said peripheral surface.

2. A drive assembly as defined by claim 1 wherein said peripheral surface is contoured to conform to the surface of said probe carrier.

3. A drive assembly as defined by claim 2 wherein said means for urging said probe carrier comprises a pressure plate.

4. A drive assembly as defined by claim 3 wherein said pressure plate includes means for adjusting pressure whereby the surface of said probe carrier is no penetrated by the tips of said wires.

5. A drive assembly as defined by claims 2 or 3 wherein said pressure plate includes a contoured low friction surface for receiving a probe carrier.

6. A drive assembly as defined by claim 5 wherein said means for coupling comprises a gear speed reducer mounted to said motor and said pressure plate is mounted to said gear speed reducer.

7. A drive assembly as defined by claim 6 wherein said wires are mounted to said drive wheel between opposing support discs.

8. A drive assembly as defined by claim 6 wherein said wires are bonded together by adhesive means.

9. A drive assembly as defined by claim 1 wherein said wires are mounted to said drive wheel between support discs.

10. A drive assembly as defined by claim 1 wherein said wires are bonded together by adhesive means.

11. A drive wheel for use with a drive assembly for a probe carrier and the like comprising a hub, a plurality of wires radially mounted about said hub, a peripheral surface defined by tips of said wires for engaging a probe carrier, and adhesive means embedding said wires whereby only said tips of said wires are exposed at said peripheral surface.

12. A drive wheel as defined by claim 11 wherein said peripheral surface is contoured to conform to the surface of a probe carrier.

* * * * *